United States Patent [19]

Jones et al.

[11] Patent Number: 4,898,997
[45] Date of Patent: Feb. 6, 1990

[54] HALOPHENYLETHYLENES

[75] Inventors: Raymond V. H. Jones, Linlithgow; Ian G. C. Fleming, Kirkliston, both of Scotland

[73] Assignee: Imperial Chemical Industries PLC, London, England

[21] Appl. No.: 287,628

[22] Filed: Dec. 20, 1988

Related U.S. Application Data

[63] Continuation of Ser. No. 862,656, May 13, 1986, abandoned, which is a continuation of Ser. No. 675,469, Nov. 28, 1984, abandoned, which is a continuation of Ser. No. 370,813, Apr. 22, 1982, abandoned.

[30] Foreign Application Priority Data

May 12, 1981 [GB] United Kingdom ................ 8114395

[51] Int. Cl.$^4$ ..................... C07C 17/24; C07C 21/18; C07C 33/24
[52] U.S. Cl. .................................... 570/128; 568/809; 570/142
[58] Field of Search ......................................... 570/128

[56] References Cited

U.S. PATENT DOCUMENTS 4,414,210 11/1983 Miller et al. ........................ 424/245
4,551,469 11/1985 Parry et al. .......................... 514/383

OTHER PUBLICATIONS

Dalton, David R. Ved P. Dutta and Daniel C. Jones "Bromohydrin Formation in Dimethyl Sulfoxide", J. Am. Chem. Soc. 90:20/Sep. 25, 1968.

*Primary Examiner*—J. E. Evans
*Attorney, Agent, or Firm*—Cushman, Darby & Cushman

[57] ABSTRACT

These compounds have the general formula:

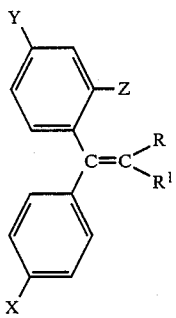

wherein R and R$^1$, which may be the same or different, are hydrogen or alkyl, preferably C$_1$–C$_4$ alkyl, and X, Y and Z are each independently hydrogen, chlorine or fluorine, provided that when R, R$^1$ and Z are hydrogen, X and Y are not both hydrogen or both fluorine, and are prepared by dehydrating an alcohol of the formula:

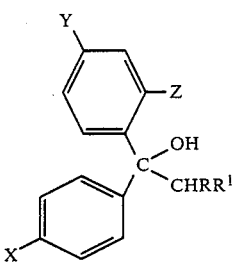

by, for example, heating the alcohol in the presence of a catalytic amount of a strong acid such as p-toluenesulphonic acid and preferably in the presence of an inert solvent.

The compounds are intermediate for the preparation of fungicidal compounds.

3 Claims, No Drawings

HALOPHENYLETHYLENES

This is a continuation of application Ser. No. 06/862,656, filed May 13, 1986, now abandoned, which in turn is a continuation of Ser. No. 675,469, filed 11/28/84, now abandoned, which in turn is a continuation of Ser. No. 370,813, filed 4/22/82, now abandoned.

This invention related to alkenes, more particularly to 1,1-diphenylalk-1-enes, and to processes for their preparation.

According to the present invention there are provided 1,1-di(optionally substituted)phenylalk-1-enes of the general formula (I):

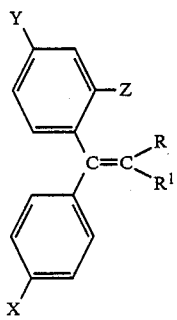

(I)

wherein R and $R^1$, which may be the same or different, are hydrogen or alkyl, preferably $C_1$–$C_4$ alkyl, and X, Y and Z are each independently hydrogen, chlorine or fluorine, provided that when R, $R^1$ and Z are hydrogen, X and Y are not both hydrogen or both fluorine.

It is preferred that at least one of X, Y and Z is chlorine or fluorine. It is further preferred that R and $R^1$ are both hydrogen.

According to a further feature of the invention there is provided a process for the preparation of the compounds of formula (I) which comprise dehydrating an alcohol of the general formula (II):

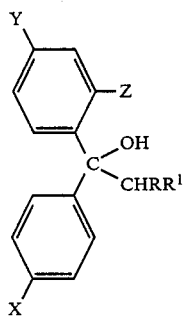

(II)

wherein R, $R^1$ X, Y and Z have the previously defined meanings.

The dehydration may be carried out by methods known from the literature for such reactions, for example, by heating the alcohol of formula (II) in the presence of a catalytic amount of a strong acid such as p-toluene-sulphonic acid, preferably in the presence of an inert solvent.

The alcohols of formula (II) may themselves be obtained by a Grignard reaction between an alkyl magnesium halide of formula (III):

$RR^1HCMg.Hal$     (III)

and a benzophenone of formula (IV):

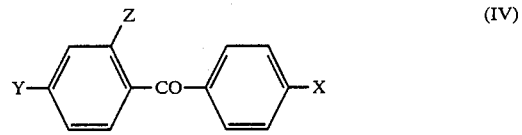

(IV)

wherein R, $R^1$, X, Y and Z have the previously defined meanings and Hal is chlorine, bromine or iodine. It is not necessary to isolate the alcohol of formula (II) before converting it into the alkene of formula (I). Thus, the alkyl magnesium halide of formula (III) may first be prepared in known manner by reaction of an alkyl halide of formula (V)

$RR^1HC.Hal$     (V)

wherein R, $R^1$ and Hal have the previously defined meanings, with metallic magnesium in an anhydrous ether solvent, for example, diethyl ether or tetrahydrofuran, optionally in admixture with a inert organic solvent such as toluene, and generally with the application of gentle heat to assist completion of the reaction. The benzophenone of formula (IV) is then added, preferably as a solution in an inert organic solvent such as toluene, to the solution of the Grignard reagent, the reaction temperature being kept at or slightly, above normal room temperature, for example, at 25°–30° C.

The reaction mixture is then poured into dilute aqueous sulphuric acid solution, the organic layer containing the tertiary alcohol of formula (II) is collected, p-toluene-sulphonic acid is added and the solution is heated to effect dehydration of the tertiary alcohol layer. When toluene is the solvent, it is convenient to conduct the dehydration at the boiling point of the solution and to remove the water with cohobation of the solvent, for example, by using a Dean and Stark apparatus. The alkene which remains in solution may then be isolated by removal of the solvent by evaporation or distillation.

The alcohol of formula (II) may also be obtained by reacting a compound of formula (VI):

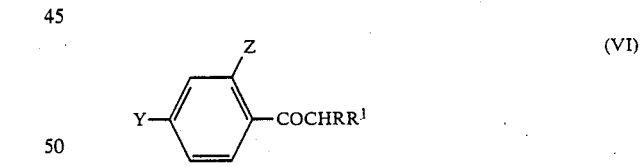

(VI)

with a Grignard compound of formula (VII):

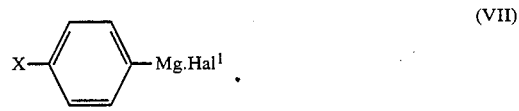

(VII)

wherein R, $R^1$, X, Y and Z have the previously defined meanings and $Hal^1$ is bromine or iodine, the reaction being conducted essentially as described previously. Again the alcohol of formula (II) need not be isolated but may be converted directly into an alkene of formula (I) as already described.

The alcohol of formula (II) in which X and Y are the same and Z is hydrogen may also be obtained by reacting 2 mol proportions of a Grignard compound of formula (VII) with 1 mol proportion of an ester of formula (VIII):

RR¹CH.COOR² (VIII)

wherein R and R¹ have the previously defined meanings and R² is a hydrocarbon radical, preferably an alkyl radical and particularly a ($C_1$-$C_4$) alkyl radical.

An example of an ester of formula (VIII) which may be used in ethyl acetate.

In this case also the alcohol of formula (II) may be converted directly into an alkene of formula (I) without an intermediate isolation step.

The alkenes of formula (I) are useful intermediates for fungicides. Those in which R=R¹=H are intermediates for the preparation of fungicidal compounds of formula (IX):

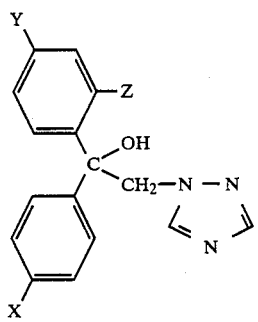

wherein X, Y and Z have the previously derived meanings compounds of formula (IX) and methods for their preparation are described in Eurpoean Patent Publication No. 15756.

The alkenes of formula (I) in which R=R¹=H may be converted to compounds of formula (IX), for example, by reaction with chloride, bromine, hypochlorous acid or hypobromous acid in aqueous medium to give the corresponding halohydrin of formula (X):

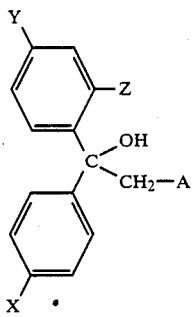

wherein X, Y and Z have the previously defined meanings and A is chlorine or bromine. The halohydrin is subsequently reacted with 1,2,4-triazole to give the compound of formula (IX) via the epoxide of formula (XI);

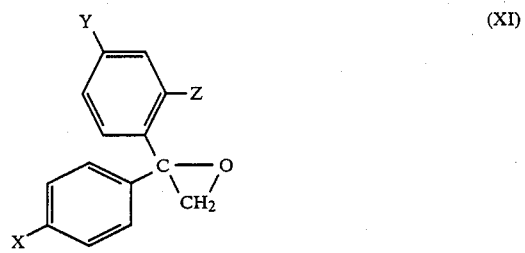

which is readily formed under the basic conditions of the triazole addition.

Particularly useful alkenes of formula (I) for the synthesis of compound of formula (IX) are those having R=R¹=H and the following substitution patterns for X, Y and Z:

| X  | Y | Z  |
|----|---|----|
| F  | H | F  |
| F  | H | Cl |
| Cl | H | Cl |
| Cl | F | H  |
| F  | Cl| Cl |

The invention is illustrated by the following Examples in which parts and percentages are by weight.

EXAMPLE 1

1-(2-chlorophenyl)-1-(4-fluorophenyl)ethene

A solution of methyl bromide (89 parts) in toluene (43 parts) is added, over about 30 minutes, to a stirred mixture of magnesium turnings (20 parts), toluene (130 parts and tetrahydrofuran (122 parts), maintaining the temperature at 30°-40° C. After the magnesium is dissolved, 2-chloro-4'-fluorobenzophenone (130 parts) in toluene (125 parts) is added, whist maintaining the temperature at 25°-30° C. The mixture is drowned out in N/1 $H_2SO_4$ (1500 parts) and stirred for 30 minutes. The organic layer is separated and p-toluenesulphonic acid (0.5 parts) is added. The solution is heated to reflux and water is completely removed with cohobation of the solvent. Removal of the solvent under vacuum leaves a brown oil (120 parts) containing 91.6% 1-(2-chlorophenyl)-1-(4-fluorophenyl)ethene (by GLC; 10% SE30 at 200° C.) (85% conversion based on 2-chloro-4'-fluorobenzophenone). Recrystallisation from ethyl acetate gives pure 1-(2-chlorophenyl)-1-(4-fluorophenyl)ethene (m.pt. 73°-74° C.).

(Found: 72.3% C; 4.3% H; 15.6% Cl; 7.9% F. $C_{14}H_{10}ClF$ requires: 72.3% C; 4.3% H; 15.2% Cl; 8.2% F.).

P.m.r. spectrum: ($CDCl_3$/TMS): 5.19 (1H: singlet); 5.67 (1H: singlet); 6.70-7.45 (8H: aromatic complex).

The 2-chloro-4'-fluorobenzophenone used in this Example was obtained by a Friedel-Crafts reaction between fluorobenzene and 2-chlorobenzoyl chloride using an aluminium chloride catalyst.

EXAMPLE 2

1-(2-fluorophenyl)-1-(4-fluorophenyl)ethene

The procedure described in Example 1 is repeated except that the 130 parts of 2-chloro-4'-fluorobenzophenone are replaced by 168 parts of 2,4'-difluorobenzophenone, which was converted into the title compound in 85% yield. Distillation, under vacuum, gives a colourless liquid which is pure 1-(2-fluorophenyl)-1-(4-fluorophenyl)ethene (b.pt. 82°/0.2 mm Hg).

(Found: 77.7% C; 4.6% H; 17.5% F; $C_{14}H_{10}F_2$ requires: 77.8% C; 4.7% H; 17.6% F).

P.m.r. spectrum: ($CDCl_3$/TMS): 5.35 (1H: singlet); 5.63 (1H: singlet); 6.75-7.45 (8H: aromatic complex).

The 2,4'-difluorobenzophenone used in this Example was obtained by a Friedel-Crafts reaction between fluorobenzene and 2-fluorobenzoyl chloride using an aluminium chloride catalyst.

We claim:
1. 1-(2-chlorophenyl)-1-(4-fluorophenyl)ethane.
2. 1-(2-fluorophenyl)-1-(4-fluorophenyl)ethane.
3. 1-(2,4-dichlorophenyl)-1-(4-fluorophenyl)ethane.

* * * * *

UNITED STATES PATENT AND TRADEMARK OFFICE
CERTIFICATE OF CORRECTION

PATENT NO.   : 4,898,997
DATED        : February 6, 1990
INVENTOR(S)  : JONES ET AL It is certified that error appears in the above-identified patent and that said Letters Patent is hereby corrected as shown below:

Column 4, line 66, change "ethane" to -- ethene --.
Column 4, line 67, change "ethane" to -- ethene --.
Column 4, line 68, change "ethane" to -- ethene --.

Signed and Sealed this

Sixteenth Day of July, 1991

Attest:

HARRY F. MANBECK, JR.

Attesting Officer

Commissioner of Patents and Trademarks